United States Patent
Cho et al.

(10) Patent No.: US 12,102,411 B2
(45) Date of Patent: Oct. 1, 2024

(54) METHOD FOR PREDICTING INTENTION OF USER AND APPARATUS FOR PERFORMING SAME

(71) Applicants: SEOUL NATIONAL UNIVERSITY R&DB FOUNDATION, Seoul (KR); KOREA ADVANCED INSTITUTE OF SCIENCE AND TECHNOLOGY, Daejeon (KR)

(72) Inventors: Kyu-Jin Cho, Seoul (KR); Sungho Jo, Daejeon (KR); Byunghyun Kang, Seoul (KR); Daekyum Kim, Daejeon (KR); Hyungmin Choi, Seoul (KR); Kyu Bum Kim, Daejeon (KR)

(73) Assignees: SEOUL NATIONAL UNIVERSITY R&DB FOUNDATION, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 284 days.

(21) Appl. No.: 17/246,299

(22) Filed: Apr. 30, 2021

(65) Prior Publication Data
US 2021/0256250 A1 Aug. 19, 2021

Related U.S. Application Data

(63) Continuation of application No. PCT/KR2019/014855, filed on Nov. 4, 2019.

(30) Foreign Application Priority Data

Nov. 2, 2018 (KR) .................. 10-2018-0133652
Nov. 4, 2019 (KR) .................. 10-2019-0139747

(51) Int. Cl.
*G06K 9/00* (2022.01)
*A61B 5/00* (2006.01)
(Continued)

(52) U.S. Cl.
CPC ............. *A61B 5/0077* (2013.01); *A61H 1/02* (2013.01); *G06N 3/08* (2013.01); *G06T 7/20* (2013.01);
(Continued)

(58) Field of Classification Search
CPC ....................................... G06V 40/28
See application file for complete search history.

(56) References Cited

U.S. PATENT DOCUMENTS

2009/0234529 A1\* 9/2009 Sampedro Diaz ...... G06F 9/451
706/14
2010/0168998 A1\* 7/2010 Matsunaga ........... B60W 30/10
701/532
(Continued)

FOREIGN PATENT DOCUMENTS

JP 2005-242759 A 9/2005
JP 2007-115236 A 5/2007
(Continued)

OTHER PUBLICATIONS

International Search Report of PCT/KR2019/014855 dated Mar. 2, 2020 [PCT/ISA/210].
(Continued)

*Primary Examiner* — Hadi Akhavannik
(74) *Attorney, Agent, or Firm* — Sughrue Mion, PLLC

(57) ABSTRACT

A method for predicting the intention of a user through an image acquired by capturing the user includes: receiving an image acquired by capturing a user; and predicting the intention of the user for the next motion by using spatial information and temporal information about the user and a target object included in the image.

13 Claims, 8 Drawing Sheets

(51) Int. Cl.
    *A61H 1/02*      (2006.01)
    *G06N 3/08*      (2023.01)
    *G06T 7/20*      (2017.01)
    *G06T 7/70*      (2017.01)
    *G06V 40/20*     (2022.01)

(52) U.S. Cl.
    CPC ............. *G06T 7/70* (2017.01); *G06V 40/20*
         (2022.01); *G06V 40/28* (2022.01); *A61H*
         *2201/5007* (2013.01); *A61H 2201/5092*
         (2013.01); *G06T 2207/20081* (2013.01); *G06T*
         *2207/20084* (2013.01); *G06T 2207/30196*
         (2013.01); *G06T 2207/30241* (2013.01)

(56) References Cited

U.S. PATENT DOCUMENTS

2013/0131985 A1* 5/2013 Weiland ................ G01C 21/20
                                                340/4.12
2018/0053108 A1* 2/2018 Olabiyi ................. G06N 3/044
2018/0075659 A1* 3/2018 Browy ................. G02B 27/017
2019/0038222 A1* 2/2019 Krimon ................ A61B 5/1107

FOREIGN PATENT DOCUMENTS

| | | |
|---|---|---|
| JP | 2008-254122 A | 10/2008 |
| JP | 2015-036915 A | 2/2015 |
| KR | 10-2008-0078217 A | 8/2008 |
| KR | 10-2016-0059844 A | 5/2016 |

OTHER PUBLICATIONS

Biplab Ketan Chakraborty et al., "Review of constraints on vision-based gesture recognition for human-computer interaction", IET Computer Vision, 2018, vol. 12, Issue 1, pp. 3-15 (13 pages).

* cited by examiner

METHOD FOR PREDICTING INTENTION OF USER AND APPARATUS FOR PERFORMING SAME

TECHNICAL FIELD

The embodiments disclosed herein relate to a method and apparatus for predicting the intention of a user through the analysis of an image acquired by capturing the user.

Year 2019 Project Number and Acknowledgement
1. Project Serial No.: 1711081714
2. Acknowledgement: This research was conducted as a result of research by the Korean Ministry of Science and ICT and the Soft Robotics Research Center of the National Research Foundation of Korea (NRF2016R1A5A1938472).

BACKGROUND ART

People usually think of the idea of performing a motion before performing it. In other words, a person has an intention for the next motion, and then performs a target motion according to the intention. For example, when a cup is placed in front of a user, the user has the idea of grasping the cup, i.e., an intention for 'grasping,' and then performs the motion of grasping the cup.

However, in the case of a user with a disorder such as quadriplegia, even when the user has an intention for a specific motion, the intention is not appropriately transmitted to the muscles, so that his or her intention is not desirably reflected in a motion. Accordingly, there are being used robots that identify intentions of users with limited mobility and assist in activities of daily living (ADL) according to the identified intentions. These robots identify an intention by detecting bio-signals such as an electroencephalogram (EEG), an electromyogram (EMG), or an electrooculogram (EOG) from a user through a sensor, or identify the intention of a person for the next motion through a mechanical signal that is detected when the user performs an action such as pressing a button.

When the above-described method of identifying an intention is used, a disadvantage arises in that cumbersomeness occurs because equipment for signal detection is complicated or in that inconvenience occurs because a user needs to perform an additional operation such as pressing a button.

Meanwhile, the above-described background technology corresponds to technical information that has been possessed by the present inventor in order to contrive the present invention or that has been acquired in the process of contriving the present invention, and can not necessarily be regarded as well-known technology that had been known to the public prior to the filing of the present invention.

DISCLOSURE

Technical Problem

The embodiments disclosed herein are intended to provide a method for accurately predicting the intention of a user through a simple operation of analyzing an image acquired by capturing the user.

Technical Solution

A method for predicting the intention of a user through an image acquired by capturing the user includes: receiving an image acquired by capturing a user; and predicting the intention of the user for the next motion by using spatial information and temporal information about the user and a target object included in the image.

Advantageous Effects

According to any one of the above-described technical solutions, there may be expected the effect of accurately predicting the intention of a user for the next motion through a simple operation of analyzing an image acquired by capturing the user.

In particular, when a user only wears a first-person point-of-view camera for image capture without wearing equipment such as a sensor for detecting a bio-signal or performing an additional operation such as pressing a button to indicate his or her intention, the intention of the user may be accurately predicted, and the user may receive assistance with a corresponding motion.

The effects that can be obtained by the embodiments disclosed herein are not limited to the above-described effects, and other effects that have not been described above will be apparently understood by those of ordinary skill in the art, to which the present invention pertains, from the following description.

BEST MODE

Figure 1:
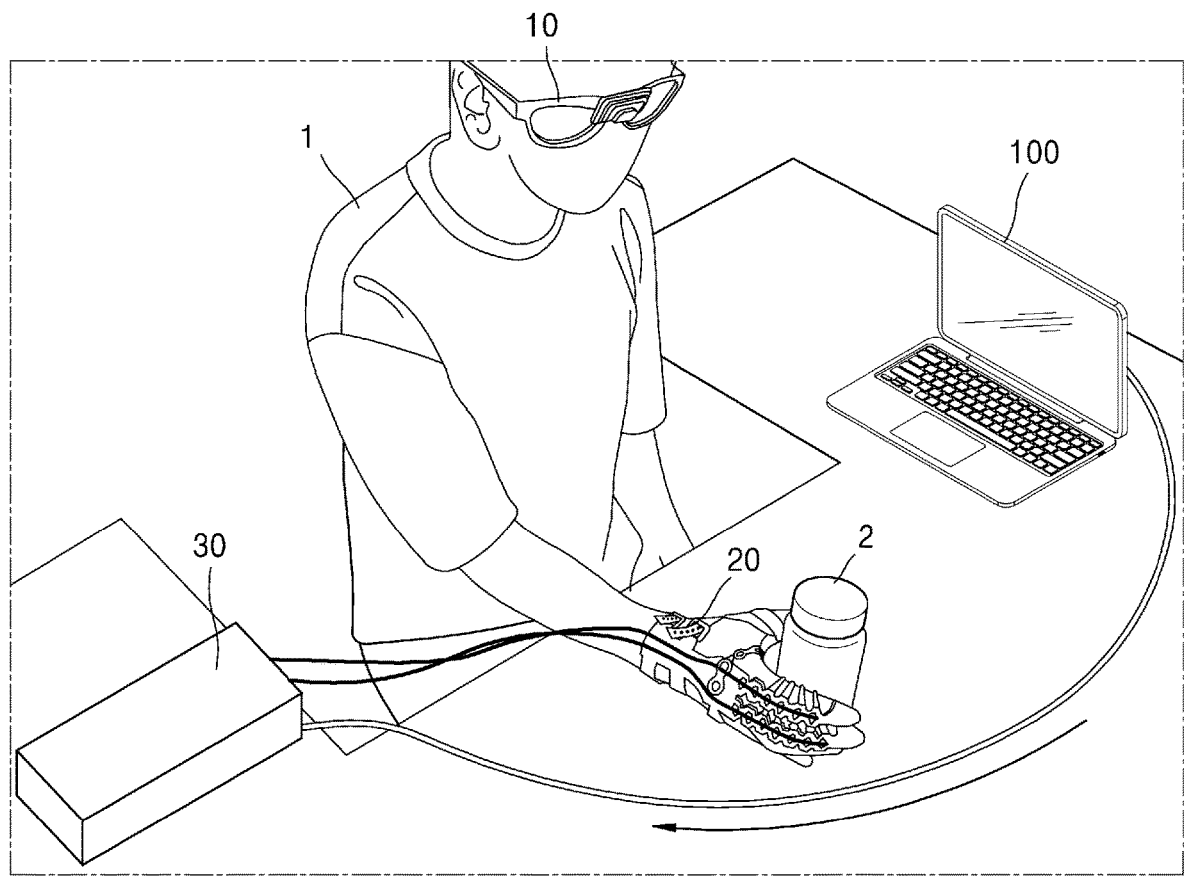
FIG. 1 is a diagram showing an intention prediction apparatus and a motion assistance system including the same according to an embodiment.

As a technical solution for solving the above-described technical problem, according to an embodiment, there is provided a method for predicting the intention of a user through an image acquired by capturing the user, the method including: receiving an image acquired by capturing a user; and predicting the intention of the user for the next motion by using spatial information and temporal information about the user and a target object included in the image.

According to another embodiment, there is provided a computer program for performing a method for predicting the intention of a user through an image acquired by capturing the user, wherein the method includes receiving an image acquired by capturing a user, and predicting the intention of the user for the next motion by using spatial information and temporal information about the user and a target object included in the image.

According to still another embodiment, there is provided a computer-readable storage medium having stored thereon a program that performs a method for predicting the intention of a user through an image acquired by capturing the user, wherein the method includes receiving an image acquired by capturing a user, and predicting the intention of the user for the next motion by using spatial information and temporal information about the user and a target object included in the image.

According to still another embodiment, there is provided an apparatus for prediction an intention, the apparatus including: an input/output unit configured to receive an image acquired by capturing a user from the outside and to output the intention of the user for the next motion predicted by analyzing the image; a storage unit configured to store a program for predicting the intention of the user for the next motion by analyzing the image; and a control unit including at least one processor; wherein the control unit predicts the intention of the user for the next motion using spatial information and temporal information about the user and a target object, included in the image, by executing the program.

MODE FOR INVENTION

Various embodiments will be described in detail below with reference to the accompanying drawings. The following embodiments may be modified to and practiced in various different forms. In order to more clearly illustrate the features of the embodiments, detailed descriptions of items that are well known to those of ordinary skill in the art to the following embodiments pertain will be omitted. In the drawings, portions unrelated to the following description will be omitted. Throughout the specification, like reference symbols will be assigned to like portions.

Throughout the specification, when one component is described as being "connected" to another component, this includes not only a case where they are 'directly connected' to each other but also a case where they are 'connected to each other with a third component disposed therebetween.' Furthermore, when a component is described as "including" another component, this does not mean that the former component excludes another component but means that the former component may further include another component, unless explicitly described to the contrary.

The embodiments will be described in detail below with reference to the accompanying drawings.

FIG. 1 is a diagram showing an intention prediction apparatus and a motion assistance system including the same according to an embodiment. Referring to FIG. 1, a motion assistance system according to an embodiment includes a camera 10, a motion assistance device 20, a driving device 30, and an intention prediction apparatus 100.

In the following, referring to FIG. 1, as an example, there will be described a situation in which when a user 1 grasps or releases a target object 2 while wearing the glove-shaped motion assistance device 20, the intention of the user for 'grasping,' 'releasing' or 'rest' is predicted by analyzing an image, captured through the camera 10, using the intention prediction apparatus 100, and the motion assistance device 20 is operated by applying a driving signal to the driving device 30 according to the predicted intention.

The camera 10 may capture the user and transmit the captured image to the intention prediction apparatus 100. The camera 10 shown in FIG. 1 may be worn by the user 1 in the form of glasses, and may capture an image from a first-person point of view. Since the camera 10 captures an image from a first-person point of view, the image may be captured such that a body part of the user 1, such as a hand or foot of the user 1, appears in the image. Meanwhile, alternatively, a camera may be worn on another body part of the user 1, or there may be used a camera capable of capturing an image from a third-person point of view.

The motion assistance device 20 is a device for assisting the user in performing motions, and, in particular, may play the role of assisting a user with limited motion in performing motions according to his or her intentions. Although the glove-shaped motion assistance device 20 configured to be worn on a hand of the user 1 is shown in FIG. 1, it will be apparent that alternatively, the motion assistance device 20 that may be worn on one or more of other various body parts of the user 1 may be used. The motion assistance device 20 is connected to the driving device 30 and operated by the driving device 30.

The driving device 30 operates the motion assistance device 20 according to a driving signal received from the intention prediction apparatus 100. For example, the driving device 30 may operate the glove-shaped motion assisting device 20 to be bent when receiving a driving signal corresponding to 'grasping' from the intention prediction device 100, and conversely, may operate the glove-shaped motion assisting device 20 to be opened when receiving a driving signal corresponding to 'releasing.'

The intention prediction apparatus 100 is a computing apparatus capable of performing operations, and may be implemented as, e.g., a PC, a notebook computer, or an embedded computing apparatus implemented to perform tasks of various purposes. The intention prediction apparatus 100 may predict an intention for the next motion of the user 1 by analyzing the captured image received from the camera 10. More specifically, the intention prediction apparatus 100 may predict an intention for the next motion of the user by using spatial information and temporal information about the user 1 and the target object 2 included in the received image. In this case, the next motion of the user 1 may refer to a motion related to the target object 2. In other words, it may refer to a motion such as grasping or releasing that is performed on the target object 2 by the user 1.

Meanwhile, in the embodiment corresponding to FIG. 1, the intention prediction apparatus 100 is described as using an image captured through the camera 10 to obtain spatial information and temporal information about the user 1 and the target object 2. Alternatively, various types of mechanical sensors including an Inertial Measurement Unit (IMU) sensor may be mounted on at least one of the user 1 and the target object 2, and spatial information and temporal information may be obtained through them. When an implementation is made in this manner, the intention prediction apparatus 100 may extract spatial information and temporal information using signals received from sensors instead of analyzing an image, and may predict the intention of a user using the extracted spatial information and temporal information.

Alternatively, the intention prediction apparatus 100 may obtain spatial information and temporal information by using both an image captured through the camera 10 and data received from sensors installed in at least one of the user 1 and the target object 2.

The intention prediction apparatus 100 may analyze an image and predict the intention of the user for the next motion using a deep learning network. A detailed process in which the intention prediction apparatus 100 predicts the intention of the user for the next motion through image analysis will be described in detail below with reference to FIG. 2.

Figure 2:
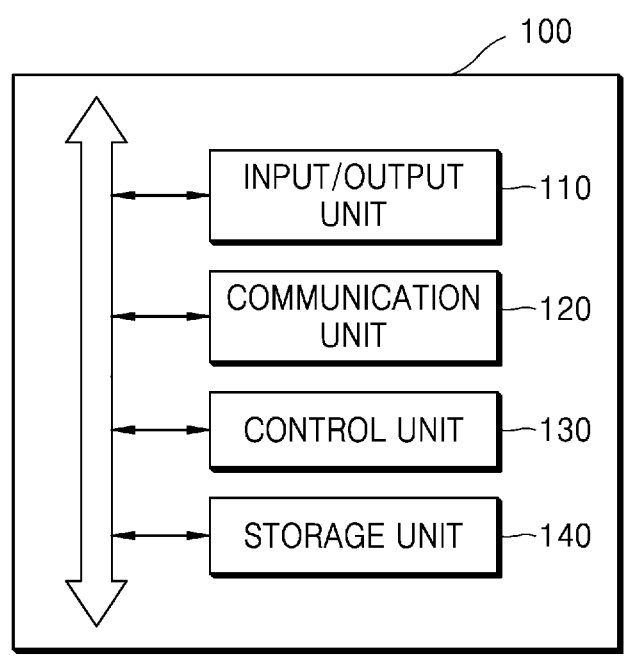
FIG. 2 is a diagram showing the detailed configuration of an intention prediction apparatus according to an embodiment.

FIG. 2 is a diagram showing the detailed configuration of an intention prediction apparatus according to an embodiment. Referring to FIG. 2, an intention prediction apparatus 100 according to an embodiment may include an input/output unit 110, a communication unit 120, a control unit 130, and a storage unit 140.

The input/output unit 110 may receive an input from the user 1 or an administrator, or may receive a captured image from the camera 10. Furthermore, the input/output unit 110 may output the intention of a user for the next motion predicted through image analysis. For example, the input/output unit 110 may output a driving signal corresponding to the predicted intention to the driving device 30.

The communication unit 120 is a component for performing wired/wireless communication with an external device, and may include various types of communication ports and a communication chipset supporting Ethernet communication, wireless LAN communication, and the like. Although the communication unit 120 is shown as a component separate from the input/output unit 110 in FIG. 2, the communication unit 120 may be included in the input/output unit 110. In other words, the communication unit 120 may operate to transmit/receive images, data, commands, and signals within the input/output unit 110 through wired/wireless communication with an external device.

Various types of programs and data may be stored in the storage unit 140. In particular, a program for predicting the intention of the user 1 for the next motion may be stored in the storage unit 140 and executed by the control unit 130 through the analysis of an image captured by the user 1.

The control unit 130 is a component including at least one processor such as a CPU, and controls the overall operation of the intention prediction apparatus 100. In particular, the control unit 130 predicts the intention of the user through image analysis by executing the program stored in the storage unit 140. For this purpose, the deep learning network shown in FIG. 3 may be implemented.

The control unit 130 may predict the intention of the user 1 for the next motion using spatial information and temporal information about the user 1 and the target object 2 included in the image received from the camera 10.

In this case, the spatial information is information about the shape, size, position, texture, stiffness, and color of an object included in an image at a stopped point of time. More specifically, it may include the pose of a body part of the user 1 and an interaction between the body part of the user 1 and the target object 2. For example, when the body part of the user 1 is a hand, the spatial information may include a gesture assumed by the hand of the user 1. Furthermore, the spatial information includes the size, shape, texture, stiffness, and color of the target object 2, so that the accuracy of prediction of an intention according to the type of target object 2 may be improved.

The interaction between the body part of the user 1 and the target object 2 included in the spatial information may include the distance between the body part of the user 1 and the target object 2 and the position and direction of the body part of the user 1. The reason for this is that the intention for the next motion may be predicted based on the distance between the hand of the user and the target object 2 and the direction in which the hand of the user approaches the target object 2 from a specific position.

Meanwhile, the temporal information includes changes in the pose and interaction of the body part of the user 1 over time. For example, how the gesture assumed by the hand of the user 1 changes over time, whether the hand of the user 1 approaches or moves away from the target 2, what is the trajectory along which the hand of the user 1 moves, and what is the speed at which the hand of the user 1 moves toward the target object 2 may be included in the temporal information.

The control unit 130 extracts spatial information and temporal information from the captured image, and uses a deep learning network to predict the intention of the user 1 for the next motion based on the extracted spatial and temporal information. In other words, a deep learning network that is implemented in such a manner that the control unit 130 executes the program stored in the storage unit 140 may receive a captured image as an input and output a predicted intention as a result value.

Figure 3:
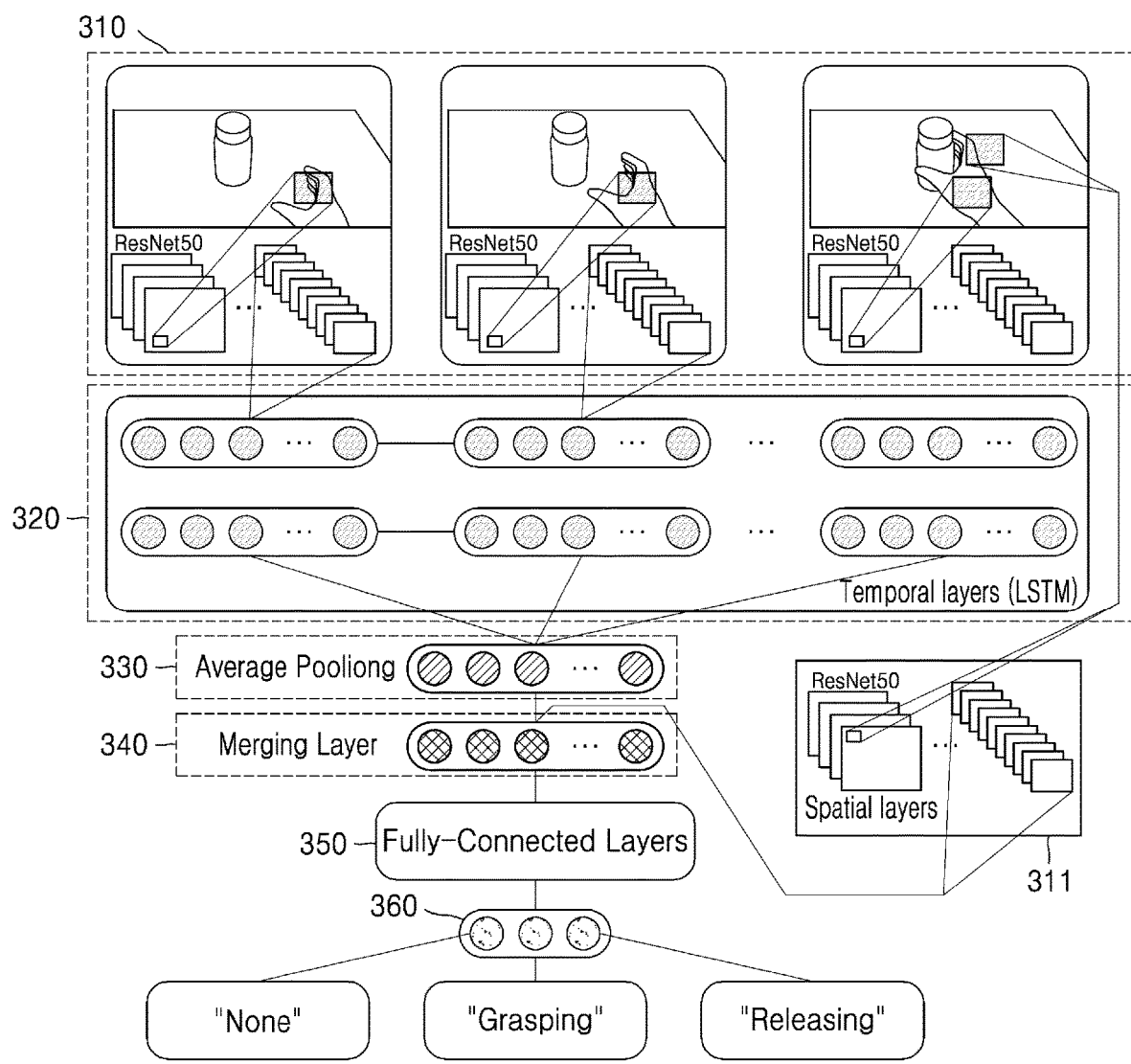
FIG. 3 is a diagram showing a deep learning network that is used when an intention is predicted through image analysis in an intention prediction apparatus according to an embodiment.

FIG. 3 is a diagram showing a deep learning network that is used when an intention is predicted through image analysis in an intention prediction apparatus according to an embodiment. Referring to FIG. 3, a deep learning network according to an embodiment may include a spatial information extraction unit 310, a temporal information extraction unit 320, a pooling layer 330, a merging layer 340, fully-connected layers, and an output unit 360.

The spatial information extraction unit 310 extracts features of spatial information for each of a plurality of frames constituting the image. Accordingly, the spatial information extraction unit 310 may be implemented as a convolution neural network (CNN) suitable for the learning and testing of two-dimensional (2D) image data. The spatial information extraction unit 310 may extract features of spatial information from pixel data included in each frame and transfer the extracted features to the temporal information extraction unit 320.

The temporal information extraction unit 320 may extract features of temporal information included in consecutive frames from the features of the spatial information received from the spatial information extraction unit 310. Accordingly, the temporal information extraction unit 320 may be implemented as a recurrent neural network (RNN) suitable for the learning and testing of time series data. In FIG. 3, in particular, there is shown an example in which the temporal information extraction unit 320 is implemented using long short-term memory (LSTM).

The pooling layer 330 may perform the task of integrating the features of the temporal information received from the temporal information extraction unit 320, and may use various pooling methods. In FIG. 3, there is shown an example in which an average pooling method is used.

The merging layer 340 integrates the features 311 of the temporal information integrated in the pooling layer 330 and the features 311 of the spatial information output from the spatial information extraction unit 310, and transfers the integrated information to the fully-connected layers 350.

The information processed in the fully-connected layers 350 is transmitted to the output unit 360, and the output unit 360 outputs the intention of the user 1 for the next motion as a result value.

The control unit 130 may apply a driving signal to the driving device 30 through the input/output unit 110 according to the intention of the user 1 for the next motion predicted through the deep learning network. In this case, in order to increase the accuracy of the predicted intention and the efficiency of the system, the control unit 130 may use the following two methods.

The first method is as follows. The deep learning network may output a considerably large number of results within a short period of time (e.g., 24 results per second). Accordingly, when driving signals are output in response to all result values, there may be problems in that the efficiency of the system is lowered and the accuracy of prediction is deteriorated. Accordingly, according to an embodiment, when applying a driving signal to the driving device 30, the control unit 130 may select a result value occupying a preset ratio or more from a plurality of result values output from the deep learning network for a predetermined period of time, and may apply a driving signal corresponding to the selected result value to the driving device 30. For example, when 12 or more result values, which are 50% or more of the 24 result values, correspond to 'grasping' on the assumption that the deep learning network outputs 24 result values per second, the control unit 130 may output a driving signal corresponding to 'grasping.' In this case, the predetermined period of time and the ratio may be appropriately set as necessary.

The second method is as follows. If the motions that can be performed by the user 1 are classified into two or more types, the motion that the user 1 desires to perform next is likely to be a motion of a type different from that of the motion currently performed by the user 1. Accordingly, the control unit 130 may check the type of motion currently performed by the user, may select only the intention for a motion different from the motion currently performed by the user from the intentions output as result values from the deep learning network for a predetermined period of time, and may apply a driving signal corresponding to the selected intention to the driving device 30. For example, when the type of motion currently performed by the user 1 is 'grasping,' the control unit 130 may select only the intention for another type of motion such as 'releasing,' other than 'grasping,' from the result values output from the deep learning network, and may output a driving signal corresponding thereto.

A method of training the deep learning network used in the present embodiment will be described below.

In order to train the deep learning network, data (one or more frames constituting an image) corresponding to each of intentions for 'grasping,' 'releasing,' and 'rest' need be collected, and an intention corresponding to the data need be labeled.

However, in general, in order to perform a specific motion, two or more motions occur at the same time and it is difficult to specify time points corresponding to the start and end of any one of them, so that it may be difficult to perform labeling. Accordingly, in the present embodiment, a guideline for labeling that can increase the accuracy of prediction of an intention is presented.

In the case of labeling for an intention for 'grasping,' a case where the distance between a body part of the user 1 and the target object 2 and the speed of the body part of the user 1 satisfy predetermined conditions is labeled an intention for 'grasping.' For example, a case where the distance between a hand of the user 1 and the target object 2 is shorter than 2 cm and the speed at which the hand of the user moves, i.e., the speed at which the hand of the user 1 approaches the target object 2, is zero may be labeled an intention for 'grasping.' These specific criteria may be set in various manners as necessary.

In the case of labeling for an intention for 'releasing,' a case where the position of the target object 2 and the speed of a body part of the user 1 satisfy predetermined conditions is labeled an intention for 'releasing.' For example, a case where at least a part of the target object 2 is located in contact with the ground and the speed of a hand of the user 1 holding the target object 2 is 0 for 3 frames or more is labeled an intention for 'releasing.' These specific criteria may be set in various manners as necessary.

Furthermore, in order to increase a learning effect, an infrared sensor may be installed in the motion assistance device 20, and the distance between the hand and the target object measured using this sensor may be reflected when learning is performed.

FIGS. 4 to 7 are flowcharts illustrating intention prediction methods according to embodiments. The intention prediction methods performed by the intention prediction apparatus 100 will be described below with reference to FIGS. 1 to 3 additionally.

Figure 4:
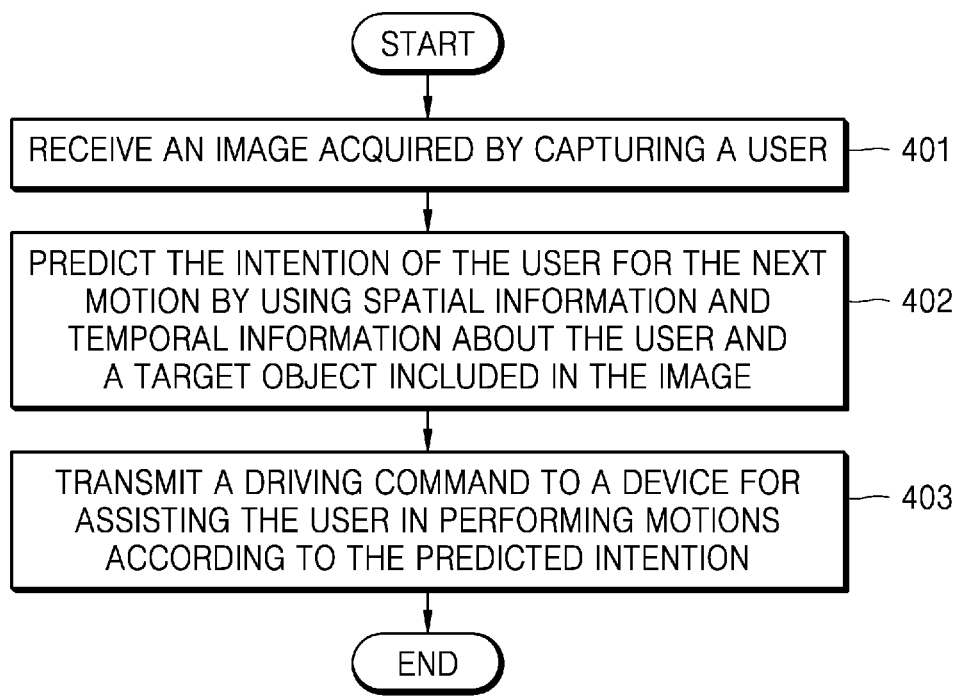
FIGS. 4 to 7 are flowcharts illustrating intention prediction methods according to embodiments.

Referring to FIG. 4, at step 401, the intention prediction apparatus 100 receives an image acquired by capturing the user 1. In this case, the received, captured image may be an image captured by the camera 10 from a first-person point of view.

At step 402, the intention prediction apparatus 100 may predict the intention of the user 1 for the next motion using spatial information and temporal information about the user 1 and the target object 2 included in the received image. A detailed process in which the intention prediction apparatus 100 predicts the intention of the user 1 through image analysis will be described in detail below with reference to FIG. 5.

At step 403, the intention prediction apparatus 100 may transmit a driving signal to the motion assistance device 20, assisting with the motion of the user, according to the intention predicted at step 402.

Figure 5:
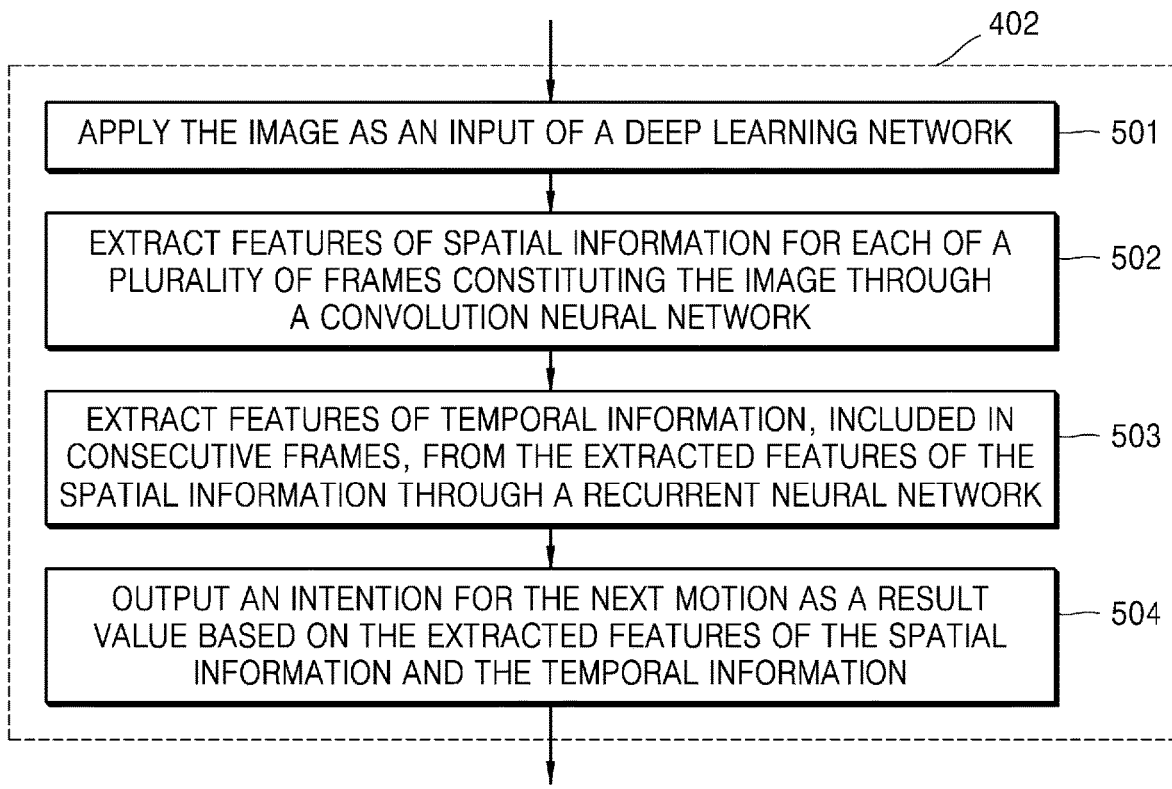

FIG. 5 is a diagram showing detailed steps included in step 402 of FIG. 4.

Referring to FIG. 5, at step 501, the control unit 130 of the intention prediction apparatus 100 applies the received image to the deep learning network as an input. The deep learning network used in this case may include the spatial information extraction unit and the temporal information extraction unit, as shown in FIG. 3.

At step 502, a convolutional neural network constituting the spatial information extraction unit of the deep learning network may extract features of spatial information for each of a plurality of frames constituting the image, and may transmit the extracted features of the spatial information to the temporal information extraction unit.

At step 503, a recurrent neural network constituting the temporal information extraction unit of the deep learning network may extract features of temporal information, included in consecutive frames, from the received features of the spatial information.

At step 504, the deep learning network may output the intention of the user 1 for the next motion as a result value based on the extracted features of the spatial information and the temporal information.

Figure 6:
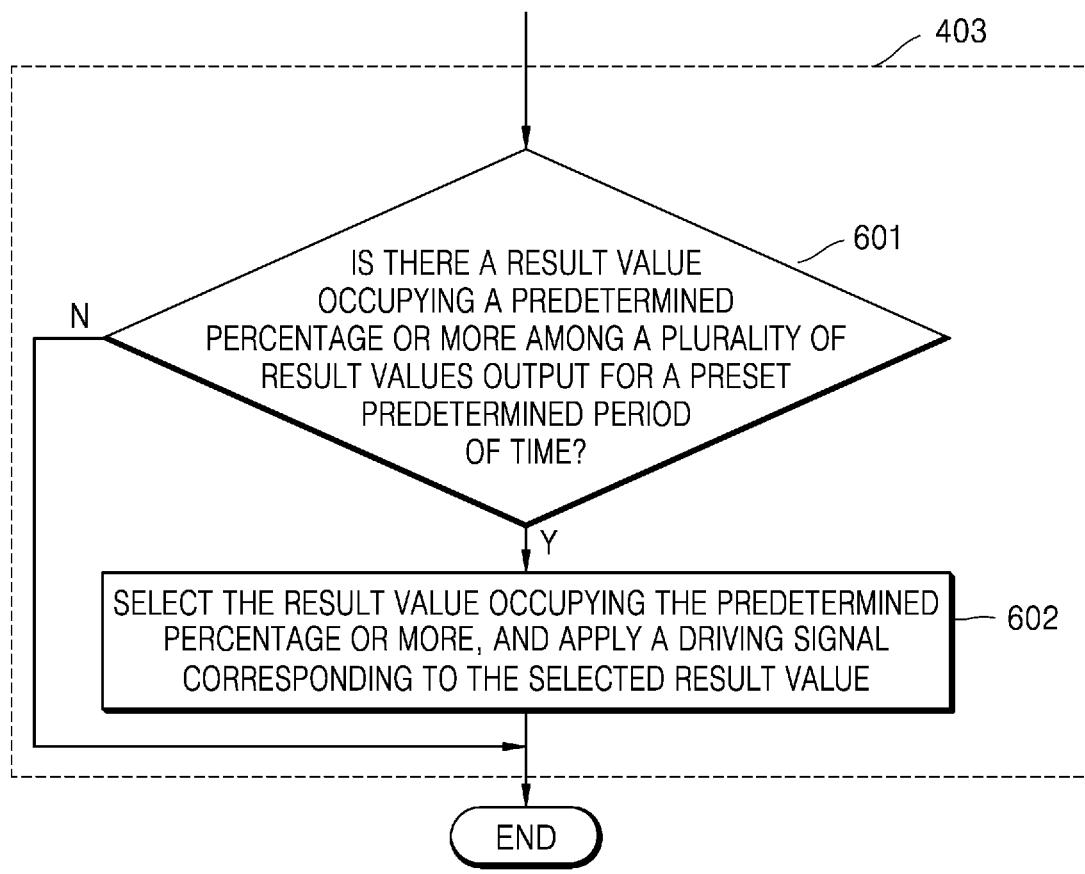

FIG. 6 is a diagram showing detailed steps included in step 403 of FIG. 4.

Referring to FIG. 6, at step 601, the control unit 130 of the intention prediction apparatus 100 determines whether there is a result value occupying a predetermined ratio or more among a plurality of result values output from the deep learning network for a predetermined period of time. If there is no result value occupying the predetermined percentage or more, the control unit terminates the process. In contrast, if there is a result value occupying the predetermined percentage or more, the process proceeds to step 602.

At step 602, the control unit 130 selects the result value occupying the predetermined ratio or more from the plurality of result values output for the predetermined period of time, and outputs a driving signal corresponding to the selected result value to the driving device 30.

Figure 7:
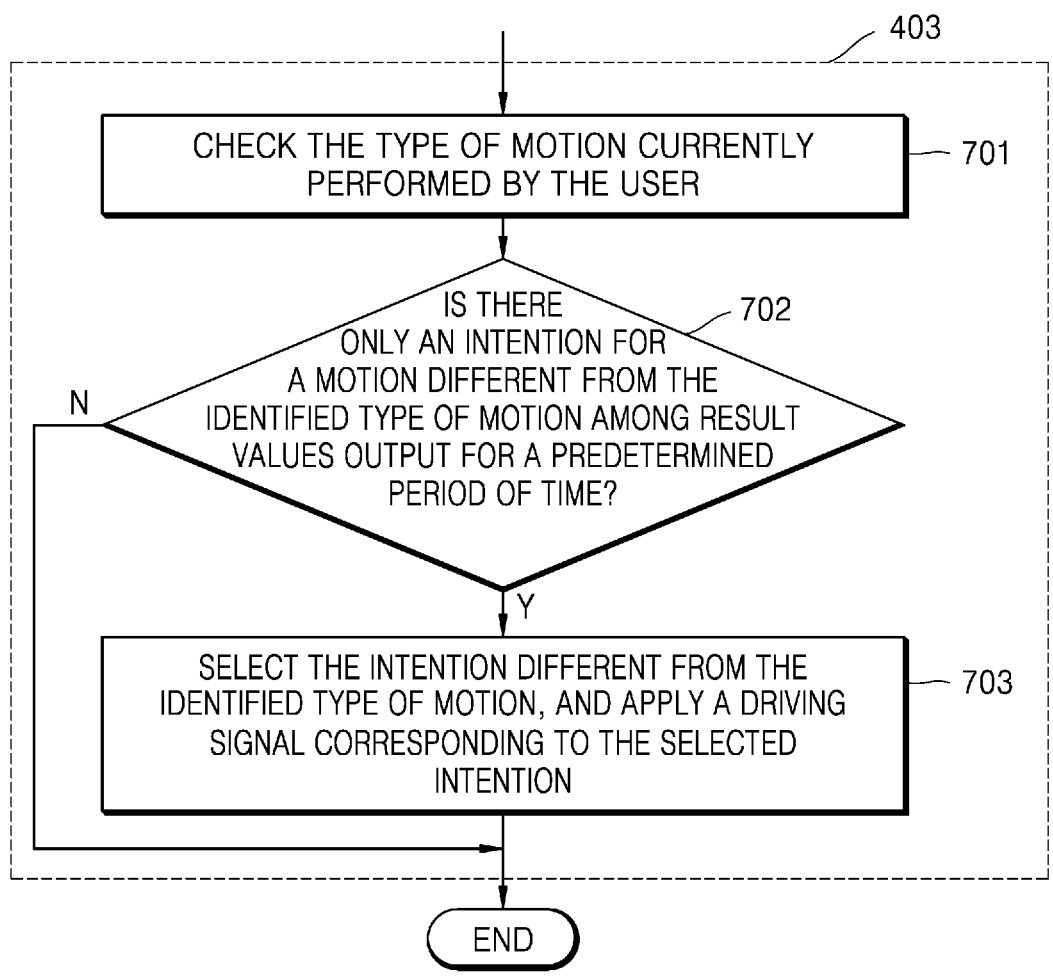

FIG. 7 is a diagram showing detailed steps included in step 403 of FIG. 4.

Referring to FIG. 7, at step 701, the control unit 130 of the intention prediction apparatus 100 checks the type of motion currently performed by the user 1.

At step 702, the control unit 130 determines whether there is an intention for a motion different from the type of motion, identified at step 701, among a plurality of result values output from the deep learning network for a predetermined period of time. If, as a result of the determination, there is no intention for a motion different from the type of motion currently performed by the user 1, the process is terminated. In contrast, if there is an intention for a motion different from the type of motion currently performed by the user 1, the process proceeds to step 703.

At step 703, the control unit 130 selects the intention for the motion different from the type of motion currently performed by the user 1, and outputs a driving signal corresponding to the selected intention to the driving device 30.

Figure 8:
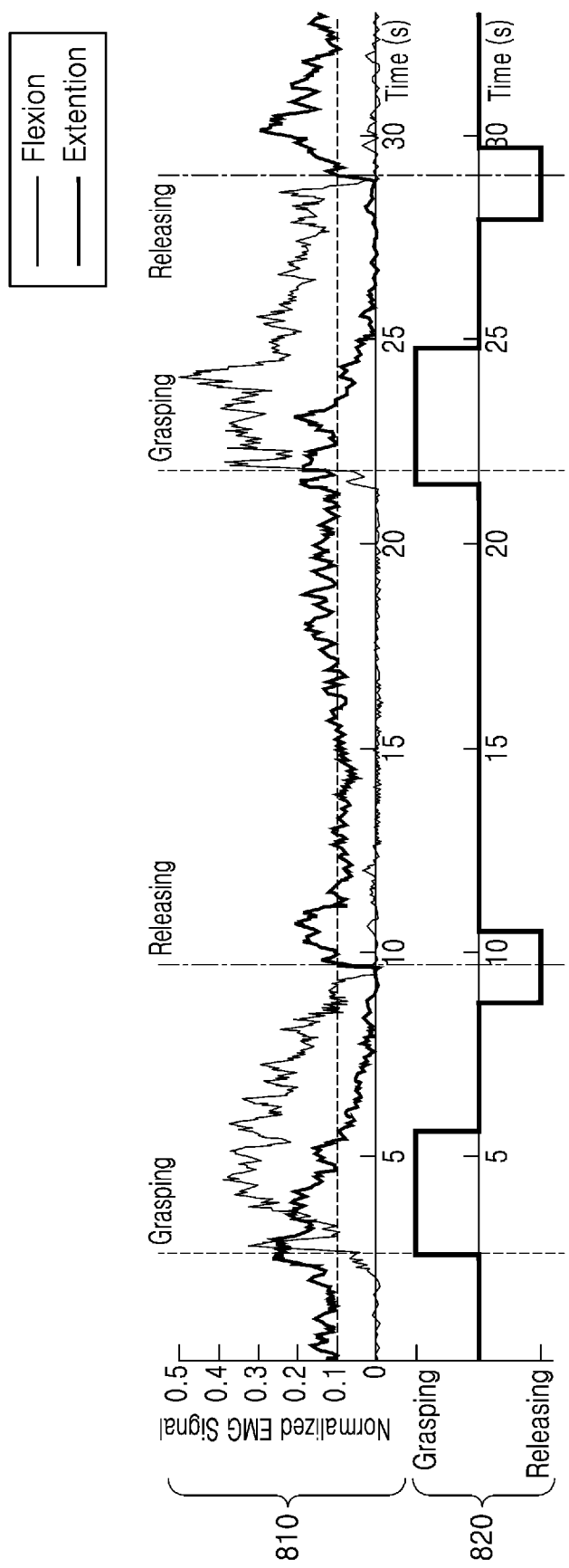
FIG. 8 is a graph showing the comparisons between the results of intention prediction using an intention prediction method and apparatus according to embodiments and the results of an intention measurement method through bio-signal detection.

FIG. 8 is a graph showing the comparisons between the results of intention prediction using an intention prediction method and apparatus according to embodiments and the results of an intention measurement method through bio-signal detection.

In the graph shown in FIG. 8, the curves plotted in an area 810 show Electromyographic (EMG) signals detected from a user. At the point where curves corresponding to flexion and extension intersect each other, it can be seen that there is an intention for 'grasping' or 'releasing.'

Meanwhile, the curve plotted in an area 820 shows the results of intention prediction through image analysis according to an embodiment, and indicates that there is an intention for either 'grasping' or 'releasing' based on a pulse waveform.

Referring to FIG. 8, it can be seen that the intention predicted through the curve plotted in the area 820 precedes the intention recognized through the curves plotted in the area 810. In other words, it can be confirmed that the intention prediction method according to the embodiment may predict intentions more accurately and faster than the conventional method.

The term 'unit' used in the above-described embodiments means software or a hardware component such as a field-programmable gate array (FPGA) or application-specific integrated circuit (ASIC), and a 'unit' performs a specific role. However, a 'unit' is not limited to software or hardware. A 'unit' may be configured to be present in an addressable storage medium, and also may be configured to run one or more processors. Accordingly, as an example, a 'unit' includes components, such as software components, object-oriented software components, class components and task components, processes, functions, attributes, procedures, subroutines, segments in program code, drivers, firmware, microcode, circuits, data, a database, data structures, tables, arrays, and variables.

Each of the functions provided in components and 'unit(s)' may be coupled to a smaller number of components and 'unit(s)' or divided into a larger number of components and 'unit (s).'

In addition, components and 'unit(s)' may be implemented to run one or more CPUs in a device or secure multimedia card.

The intention prediction method according to each of the embodiments described via FIGS. 4 to 7 may be implemented in the form of a computer-readable medium that stores instructions and data that can be executed by a computer. In this case, the instructions and the data may be stored in the form of program code, and may generate a predetermined program module and perform a predetermined operation when executed by a processor. Furthermore, the computer-readable medium may be any type of available medium that can be accessed by a computer, and may include volatile, non-volatile, separable and non-separable media. Furthermore, the computer-readable medium may be a computer storage medium. The computer storage medium may include all volatile, non-volatile, separable and non-separable media that store information, such as computer-readable instructions, a data structure, a program module, or other data, and that are implemented using any method or technology. For example, the computer storage medium may be a magnetic storage medium such as an HDD, an SSD, or the like, an optical storage medium such as a CD, a DVD, a Blu-ray disk or the like, or memory included in a server that can be accessed over a network.

Furthermore, the intention prediction method according to each of the embodiments described via FIGS. 4 to 7 may be implemented as a computer program (or a computer program product) including computer-executable instructions. The computer program includes programmable machine instructions that are processed by a processor, and may be implemented as a high-level programming language, an object-oriented programming language, an assembly language, a machine language, or the like. Furthermore, the computer program may be stored in a tangible computer-readable storage medium (for example, memory, a hard disk, a magnetic/optical medium, a solid-state drive (SSD), or the like).

Accordingly, the intention prediction method according to each of the embodiments described via FIGS. 4 to 7 may be implemented in such a manner that the above-described computer program is executed by a computing apparatus. The computing apparatus may include at least some of a processor, memory, a storage device, a high-speed interface connected to memory and a high-speed expansion port, and a low-speed interface connected to a low-speed bus and a storage device. These individual components are connected using various buses, and may be mounted on a common motherboard or using another appropriate method.

In this case, the processor may process instructions within a computing apparatus. An example of the instructions is instructions which are stored in memory or a storage device in order to display graphic information for providing a Graphic User Interface (GUI) onto an external input/output device, such as a display connected to a high-speed interface. As another embodiment, a plurality of processors and/or a plurality of buses may be appropriately used along with a plurality of pieces of memory. Furthermore, the processor may be implemented as a chipset composed of chips including a plurality of independent analog and/or digital processors.

Furthermore, the memory stores information within the computing device. As an example, the memory may include a volatile memory unit or a set of the volatile memory units. As another example, the memory may include a non-volatile memory unit or a set of the non-volatile memory units. Furthermore, the memory may be another type of computer-readable medium, such as a magnetic or optical disk.

In addition, the storage device may provide a large storage space to the computing device. The storage device may be a computer-readable medium, or may be a configuration including such a computer-readable medium. For example, the storage device may also include devices within a storage area network (SAN) or other elements, and may be a floppy disk device, a hard disk device, an optical disk device, a tape device, flash memory, or a similar semiconductor memory device or array.

The above-described embodiments are intended for illustrative purposes. It will be understood that those having ordinary knowledge in the art to which the present invention pertains can easily make modifications and variations without changing the technical spirit and essential features of the present invention. Therefore, the above-described embodiments are illustrative and are not limitative in all aspects. For example, each component described as being in a single form may be practiced in a distributed form. In the same manner, components described as being in a distributed form may be practiced in an integrated form.

The scope of protection pursued via the present specification should be defined by the attached claims, rather than the detailed description. All modifications and variations which can be derived from the meanings, scopes and equivalents of the claims should be construed as falling within the scope of the present invention.

The invention claimed is:

1. A method for predicting an intention of a user with limited motion through an image acquired by capturing the user, the method comprising:
   receiving an image acquired by capturing a target object and a body part of the user which is at least one of a hand, an arm and a foot of the user;
   predicting an intention of the user for the user's next body motion for the target object by using spatial information and temporal information about the user and the target object included in the image; and
   applying a driving signal for operating to assist the user in performing the user's next body motion corresponding to the predicted intention, to a device for assisting the user in performing the user's body motions,
   wherein the spatial information is acquired based on each of a plurality of frames constituting the image and comprises the pose of the body part of the user, the position of the target object and an interaction between the body part of the user and the target object,
   wherein the interaction comprises a distance between the body part and the target object, a position and a direction of the body part based on the target object,
   wherein the temporal information is acquired based on the spatial information and comprises a speed at which the body part moves toward the target object, changes in the pose of the body part of the user viewed by eyes of the user over time and changes in the interaction between the body part of the user and the target object over time, and
   wherein the device for assisting the user in performing the user's body motions is worn on at least one of the body parts of the user.

2. The method of claim 1, wherein the interaction comprises a position and direction of the body part based on the target object.

3. The method of claim 1, wherein the temporal information comprises at least one of a trajectory along which the body part moves.

4. The method of claim 1, wherein predicting the intention of the user comprises:
   applying the image to a deep learning network as an input;
   extracting features of the spatial information for the each of the plurality of frames constituting the image through a convolution neural network (CNN) included in the deep learning network;
   extracting features of the temporal information, included in consecutive frames, from the extracted features of the spatial information through a recurrent neural network (RNN) included in the deep learning network; and
   outputting the intention the user for the user's next body motion for the target object as a result value based on the extracted features of the spatial information and the temporal information.

5. The method of claim 4, wherein applying the driving signal comprises:
   selecting a result value occupying a predetermined percentage or more among a plurality of result values output from the deep learning network for a preset predetermined period of time; and
   applying a driving signal corresponding to the selected result value.

6. A non-transitory computer-readable recording medium having recorded thereon a program that performs the method set forth in claim 1.

7. An apparatus for prediction an intention of a user with limited motion, the apparatus comprising:
   an input/output unit configured to receive an image acquired by capturing a target object and a body part of the user which is at least one of a hand, an arm and a foot of the user from an outside and to output an intention of the user for a next motion predicted by analyzing the image;
   a storage unit configured to store a program for predicting an intention of the user for a next motion by analyzing the image; and
   a control unit including at least one processor,
   wherein the control unit predicts an intention of the user for the user's next body motion for the target object by using spatial information and temporal information about the user and the target object, included in the image, by executing the program, and applies a driving signal for operating to assist the user in performing the user's next body motion corresponding to the predicted intention, to a device for assisting the user in performing the user's body motions through the input/output unit,
   wherein the spatial information is acquired based on each of a plurality of frames constituting the image and comprises the pose of the body part of the user, the position of the target object and an interaction between the body part of the user and the target object,
   wherein the interaction comprises a distance between the body part and the target object, a position and direction of the body part based on the target object,
   wherein the temporal information comprises a speed at which the body part moves toward the target object, changes in the pose of the body part of the user viewed by eyes of the user over time and changes in the interaction between the body part of the user and the target object over time, and
   wherein the device for assisting the user in performing the user's body motions is worn on at least one of the body parts of the user.

8. The apparatus of claim 7, wherein the spatial information further comprises at least one of a size, shape, texture, stiffness, and color of the target object.

9. The apparatus of claim 7, wherein the temporal information comprises changes in the pose of the body part of the user and the interaction over time.

10. The apparatus of claim 7, wherein a deep learning network that is implemented by the control unit by executing the program and receives the image as an input comprises:
- a spatial information extraction unit configured to extract features of the spatial information for the each of the plurality of frames constituting the image;
- a temporal information extraction unit configured to extract features of the temporal information, included in consecutive frames, from the extracted features of the spatial information; and
- an intention output unit configured to output the intention for the user's next motion for the target object as a result value based on outputs of the spatial information extraction unit and the temporal information extraction unit.

11. The apparatus of claim 10, wherein the control unit, when applying the driving signal, selects a result value occupying a predetermined percentage or more among a plurality of result values output from the deep learning network for a preset predetermined period of time, and applies a driving signal corresponding to the selected result value.

12. The apparatus of claim 10, wherein:
- motions that can be performed by the user are classified into at least two types; and
- the control unit, when applying the driving signal, checks a type of motion currently performed by the user, selects only an intention for a motion different from the identified type of motion from intentions output as result values from the deep learning network for a predetermined period of time, and applies a driving signal corresponding to the selected intention.

13. The apparatus of claim 7, wherein the image acquired by capturing the user is an image that is captured from a first-person point of view of the user such that at least a body part of the user appears in the image.

* * * * *